United States Patent [19]
Theriot

[11] Patent Number: 5,861,538
[45] Date of Patent: Jan. 19, 1999

[54] PRODUCTION OF ALKOXYNAPHTHYL-SUBSTITUTED KETONES FROM NAPHTHALDEHYDES

[75] Inventor: Kevin J. Theriot, Baton Rouge, La.

[73] Assignee: Albemarle Corporation, Richmond, Va.

[21] Appl. No.: 905,526

[22] Filed: Aug. 4, 1997

[51] Int. Cl.$^6$ ................................................. C07C 45/45
[52] U.S. Cl. ............................................................. 568/313
[58] Field of Search ............................................. 508/313

[56] References Cited

U.S. PATENT DOCUMENTS

| | | | |
|---|---|---|---|
| 3,506,682 | 4/1970 | Fried | 568/313 |
| 4,061,779 | 12/1977 | Lake et al. | 424/331 |
| 4,270,004 | 5/1981 | Rose et al. | 568/314 |
| 4,420,639 | 12/1983 | Lake et al. | 568/328 |
| 5,214,151 | 5/1993 | Nakajima et al. | 568/313 |
| 5,300,654 | 4/1994 | Nakajima et al. | 568/313 |

FOREIGN PATENT DOCUMENTS 0376516  7/1990  European Pat. Off. .

OTHER PUBLICATIONS

Fieser, Louis F. et al., Organic Chemistry (1944), pp. 700–701.

*Primary Examiner*—James H. Reamer
*Attorney, Agent, or Firm*—Philip M. Pippenger

[57] ABSTRACT

A mixture formed from an alkoxy-2-naphthaldehyde (e.g., 6-methoxy-2-naphthaldehyde), acetone, and aqueous NaOH and/or KOH is heated at about 20° to about 56° C. for about 0.25 to about 2 hours such that the conversion of monoalkoxy-substituted 2-naphthaldehyde is at least 97% and the yield of (alkoxy-substituted 2-naphthyl)-3-buten-2-one is at least 95% based on the monoalkoxy-substituted 2-naphthaldehyde used in forming the mixture. The (alkoxy-substituted 2-naphthyl)-3-buten-2-one can be hydrogenated using, for example, a Pd/C catalyst to form the corresponding saturated ketone. The process enables efficient production of precursors of nabumetone and related pharmaceuticals by a clean, highly efficient reaction.

10 Claims, No Drawings

PRODUCTION OF ALKOXYNAPHTHYL-SUBSTITUTED KETONES FROM NAPHTHALDEHYDES

TECHNICAL FIELD

This invention relates to the synthesis of (alkoxy-substituted 2-naphthyl)-3-buten-2-ones and (alkoxy-substituted 2-naphthyl)-2-butanones.

BACKGROUND

U.S. Pat. Nos. 4,061,779; 4,270,004; and 4,420,639 describe, inter alia, a class of alkyl aralkyl ketones in which the aryl portion of the aralkyl group is a 2-naphthyl group having a specified substituent in the 6-position. These compounds are reported to have anti-inflammatory and/or analgesic activity, and to have the additional advantage of not excessively irritating the stomach at the therapeutic dose. Among the compounds described in these patents is the well known non-steroidal antiinflammatory agent, 4-(6-methoxy-2-naphthyl)-2-butanone, generally known as nabumetone.

While analogous compounds having a double bond in the aliphatic side chain are also reported in these patents to possess the same beneficial properties, it is further reported in the patent that the carbon-carbon double bond tends to impart a degree of oestrogenicity to these compounds. For this reason, the patent recommends using compounds which do not contain the carbon-carbon double bond. Thus the olefinically unsaturated compounds are hydrogenated to saturate the double bond, and thereby provide superior pharmaceuticals.

In Example 20 of the above patents 4-(6-methoxy-2-naphthyl)-3-buten-2-one is prepared in about 41% yield by stirring 6-methoxy-2-naphthaledehyde in excess acetone and approximately 15 mole % aqueous sodium hydroxide, followed by acidification, recovery by ether extraction, and column purification (silica gel column and benzene as eluant). As opposed to the foregoing process in which several co-products are formed in the reaction necessitating tedious separation and purification procedures, it would be highly advantageous if a way could be found for producing 4-(6-methoxy-2-naphthyl)-3-buten-2-one and related substituted 2-naphthyl ketones in an essentially single clean, high conversion and high yield reaction. This invention is deemed to fulfill this need.

Commonly-owned copending application Ser. No. 08/846,220, filed Apr. 25, 1997 by V. Ramachandran and S. E. Belmont describes, inter alia, the synthesis of (alkoxy-substituted 2-naphthyl)-3-buten-2-ones by use of a heterogeneous basic catalyst such as alumina or alkali metal hydroxide in the solid state.

SUMMARY OF THE INVENTION

In accordance with this invention there is provided a new, advantageous process for producing 4-(6-methoxy-2-naphthyl)-3-buten-2-one and related (alkoxy-substituted 2-naphthyl)-3-buten-2-ones. The process is rapid, facile and economical. It gives extremely high conversions and yields of the desired product, with only a small amount of easily-recoverable and readily-disposable co-product. The process is thus eminently suited for use on an industrial scale.

It has now been found that, contrary to the unfavorable results achieved in Example 20 of U.S. Pat. Nos. 4,061,779; 4,270,004; and 4,420,639, aqueous alkali metal hydroxide can be exceptionally effective in promoting the reaction of an alkoxy-substituted 2-naphthaldehyde with acetone provided that (a) the reaction is performed using proportions in the range of about 5 to about 20 moles of acetone and in the range of about 0.1 to about 5 moles of alkali metal hydroxide per mole of monoalkoxy-substituted 2-naphthaldehyde; and (b) the mixture formed from these ingredients is maintained and/or heated at one or more temperatures in the range of about 20° to about 56° C. for a period in the range of about 0.25 to about 3 hours (preferably in the range of about 0.25 to about 2 hours whereby typically the conversion of monoalkoxy-substituted 2-naphthaldehyde is at least about 97% and the yield of (alkoxy-substituted 2-naphthyl)-3-buten-2-one is at least about 95% based on the amount of monoalkoxy-substituted 2-naphthaldehyde ingredient introduced to the reaction. The times and temperatures of the foregoing ranges are, in general, inversely proportional to each other. Thus, when conducting the reaction at the lower temperatures of the foregoing range the time periods are usually longer than when conducting the reaction at the higher temperatures of the foregoing range. By proper conduct of the process, not only is the desired product formed with very high conversions and in very high yields, but reaction times are very short. Thus plant throughput and operational efficiency are greatly improved. Except for a small amount of a heavy co-product, the process, when operated under the appropriate conditions, can produce (alkoxy-substituted 2-naphthyl)-3-buten-2-one as essentially the only product formed in the reaction.

Accordingly, pursuant to one embodiment of this invention there is provided a process for the preparation of an (alkoxy-substituted 2-naphthyl)-3-buten-2-one which comprises:

a) mixing (i) a monoalkoxy-substituted 2-naphthaldehyde, (ii) acetone and (iii) alkali metal hydroxide solution wherein the alkali metal cation is sodium or potassium or both of them, in proportions in the range of about 5 to about 20 mole of acetone and in the range of about 0.1 to about 5 mole of alkali metal hydroxide per mole of monoalkoxy-substituted 2-naphthaldehyde; and b) heating the mixture at one or more temperatures in the range of about 20° to about 56° C. for a period in the range of about 0.25 to about 2 hours such that the conversion of monoalkoxy-substituted 2-naphthaldehyde is at least 97% and the yield of (alkoxy-substituted 2-naphthyl)-3-buten-2-one is at least 95% based on the monoalkoxy-substituted 2-naphthaldehyde ingredient used in forming the mixture in a).

When conducted pursuant to preferred conditions of this invention, conversions of 6-methoxy-2-naphthaldehyde at least as high as 97% and yields (by GC) of 4-(6-methoxy-2-naphthyl)-3-buten-2-one at least as high as 95% can be achieved.

Another embodiment of this invention is a process which comprises producing an (alkoxy-substituted 2-naphthyl)-3-buten-2-one in accordance with steps a) and b) above, and hydrogenating the olefinic double bond of the (alkoxy-substituted 2-naphthyl)-3-buten-2-one to form the (alkoxy-substituted 2-naphthyl)-2-butanone. A preferred method for effecting this selective hydrogenation (i.e., hydrogenation of the olefinic carbon-carbon double bond without excessive hydrogenation of the carbon-oxygen double bond) involves treating the unsaturated 2-naphthyl ketone with hydrogen at atmospheric or slightly elevated pressure (e.g., up to about 100 psig) at one or more temperatures in the range of about 0° to about 100° C., preferably at ambient room temperature, using a palladium/carbon catalyst such as 5% or 10% palladium on charcoal.

These and other embodiments will be still further apparent from the ensuing description and appended claims.

FURTHER DETAILED DESCRIPTION

The preferred unsaturated 2-naphthyl ketones produced in accordance with this invention have the formula:

$$Ar-CH=CH-CO-CH_3$$

where Ar is a monoalkoxy-substituted 2-naphthyl group where the substitution is in one or more of the 4, 5, 6, 7 and 8 positions, and the alkoxy substituent has 1 to 4 carbon atoms. Preferably, the alkoxy-substitution in Ar is in the 6-position, and most preferably such substituent is a methoxy group.

In the embodiments of this invention wherein the foregoing unsaturated 2-naphthyl ketones are subjected to hydrogenolysis the resultant saturated 2-naphthyl ketones have the formula:

$$Ar-CH_2-CH_2-CO-CH_3$$

where Ar, $R^1$ and $R^2$ are as described above.

A preferred method for producing the 2-naphthaldehyde or substituted 2-naphthaldehyde (ArCHO, preferably where Ar is as described above) used as the starting material in the process of this invention is to convert an unsubstituted or substituted 2-bromo or 2-chloronaphthalene (ArBr or ArCl, where Ar is as described above) to the Grignard reagent and react dimethylformamide with the Grignard reagent under suitable reaction conditions in accordance with known technology.

In conducting the reaction between the acetone and the alkoxy-substituted 2-naphthaldehyde, the acetone is used in stoichiometric excess, and on completion of the reaction the excess acetone can readily be recovered for reuse by distillation under relatively mild conditions. If desired, this reaction can be conducted in an ancillary chemically indifferent liquid solvent such as a paraffinic and/or cycloparaffinic hydrocarbon, an ether or polyether, or the like. As noted above temperatures for the reaction are in the range of about 20° to about 56° C. at ordinary ambient atmospheric pressures, and the reaction periods are in the range of about 0.25 to about 2 hours. Preferred temperatures are in the range of about 40 to about 56° C and reaction periods in the range of about 0.5 to about 1.5 hours are preferred. The reaction can be conducted at superatmospheric pressures, but ordinarily operation under ambient pressures as developed in a reactor equipped with a reflux condenser or tower is preferable.

The selective hydrogenation of the carbon-to-carbon double bond in the unsaturated 2-naphthyl ketone is typically performed in a suitable liquid medium such as, for example, ethyl acetate or other liquid lower alkyl ester of acetic or propionic acid; an alkanol such as ethanol, 1-propanol, 2-propanol, 1-butanol, 2-methyl-1-propanol, or the like; or a hydrocarbon such as pentane, hexane heptane, cyclohexane, methylcyclohexane, toluene, one or more xylenes, tetrahydronaphthalene or the like. In some cases a buffer, such as sodium acetate, potassium carbonate or sodium dihydrogen phosphate can be included in the reaction mixture.

The hydrogenation is typically conducted using hydrogen or a suitable hydrogen source such as ammonium formate, (preferably gaseous hydrogen) at atmospheric or elevated pressures (e.g., up to about 2 atmospheres) at one or more temperatures in the range of about 0° to about 60° C., preferably at ambient room temperature. The preferred catalyst is palladium on carbon, such as 5% or 10% palladium on charcoal. Reaction periods typically fall in the range of about 1 to about 15 hours.

The following examples, wherein all percentages are by weight, illustrate the practice and advantages of this invention, and are not to be construed as constituting limitations on the invention.

EXAMPLE 1

6-Methoxy-2-naphthaldehyde (1 g, 5.4 mmol) in acetone (5.0 g), with aqueous NaOH (0.25 g of 2.8% NaOH; 3.3 mol %) was stirred for 1 hour at 20° C. followed by 1 hour at reflux. Water (10 g) was added to precipitate the product which was filtered and dried to give 1.2 g (98% of theory) of 4-(6-methoxy-2-naphthyl)-3-buten-2-one. GC showed 99% conversion and 4% of a heavy co-product (95% of butenone).

EXAMPLE 2

Repetition of the procedure of Example 1 but without the 1-hour period of stirring at 20° C. gave similar results, thus indicating that a mere one-hour period of refluxing was sufficient to achieve high conversion and high yield of 4-(6-methoxy-2-naphthyl)-3-buten-2-one.

The high selectivity of the reaction between the 6-methoxy-2-naphthaldehyde and acetone such as achieved in Example 1 is surprising in light of the mixture of products formed using aqueous sodium hydroxide in the manner of Example 20 of U.S. Pat. Nos. 4,061,779; 4,270,004; and 4,420,639.

It is to be understood that the reactants and components referred to by chemical name or formula anywhere in the specification or claims hereof, whether referred to in the singular or plural, are identified as they exist prior to coming into contact with another substance referred to by chemical name or chemical type (e.g., another reactant, a solvent, or etc.). It matters not what preliminary chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. In short, the reactants and components are identified as ingredients to be brought together in connection with performing a desired chemical reaction or in forming a mixture to be used in conducting a desired reaction. Accordingly, even though the claims hereinafter may refer to substances, components and/or ingredients in the present tense ("comprises", "is", etc.), the reference is to the substance, component or ingredient as it existed at the time just before it was first contacted, formed in situ, blended or mixed with one or more other substances, components and/or ingredients in accordance with the present disclosure. Thus the fact that a substance, component or ingredient may have lost its original identity through a chemical reaction or transformation during the course of contacting, in situ formation, blending or mixing operations, if conducted in accordance with this disclosure and with the application of common sense and the ordinary skill of a chemist, is thus wholly immaterial for an accurate understanding and appreciation of the true meaning and substance of this disclosure and the claims thereof.

Each and every patent or other publication referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

What is claimed is:

1. A process for the preparation of an (alkoxy-substituted 2-naphthyl)-3-buten-2-one which comprises:
   a) mixing (i) a monoalkoxy-substituted 2-naphthaldehyde, (ii) acetone and (iii) alkali metal hydroxide solution wherein the alkali metal cation is sodium or potassium or both of them, in proportions in the range of about 5 to about 20 moles of acetone and in the range of about 0.1 to about 5 moles of alkali metal hydroxide per mole of monoalkoxy-substituted 2-naphthaldehyde; and
   b) heating the mixture at one or more temperatures in the range of about 20° to about 56° C. for a period in the range of about 0.25 to about 3 hours such that the conversion of monoalkoxy-substituted 2-naphthaldehyde is at least 97% and the yield of (alkoxy-substituted 2-naphthyl)-3-buten-2-one is at least 95% based on the monoalkoxy-substituted 2-naphthaldehyde used in a).

2. A process according to claim 1 wherein said alkali metal hydroxide solution is an aqueous sodium hydroxide solution.

3. A process according to claim 1 wherein the alkoxy group of the monoalkoxy-substituted 2-naphthaldehyde has 1 to 4 carbon atoms and is in one of the 4, 5, 6, 7 and 8 positions.

4. A process according to claim 1 wherein said alkali metal hydroxide solution is a 1 to 10 wt % aqueous sodium hydroxide solution.

5. A process according to claim 1 wherein said 2-naphthaldehyde is 6-methoxy-2-naphthaldehyde.

6. A process according to claim 1 wherein the alkoxy group of the monoalkoxy-substituted 2-naphthaldehyde has 1 to 4 carbon atoms and is in one of the 4, 5, 6, 7 and 8 positions; wherein said alkali metal hydroxide solution is an aqueous sodium hydroxide solution.

7. A process according to claim 6 wherein said 2-naphthaldehyde is 6-methoxy-2-naphthaldehyde.

8. A process according to claim 6 wherein said aqueous sodium hydroxide solution is a 1 to 10 wt % aqueous sodium hydroxide solution.

9. A process according to claim 8 wherein said 2-naphthaldehyde is 6-methoxy-2-naphthaldehyde.

10. A process according to any of claims 1–9 taken individually wherein (alkoxy-substituted 2-naphthyl)-3-buten-2-one formed is hydrogenated such that the corresponding (alkoxy-substituted 2-naphthyl)-2-butanone is produced.

* * * * *